(12) United States Patent
Islam et al.

(10) Patent No.: US 8,097,172 B2
(45) Date of Patent: Jan. 17, 2012

(54) RECOVERY OF ORGANIC COMPOUNDS USING A SATURATOR

(75) Inventors: Muhammad Nazrul Islam, Sugarland, TX (US); Gwo-Jang Abraham Liou, Houston, TX (US); Stephen D. York, Missouri City, TX (US)

(73) Assignee: Aker Kvaerner, Inc., Houston, TX (US)

( * ) Notice: Subject to any disclaimer, the term of this patent is extended or adjusted under 35 U.S.C. 154(b) by 1000 days.

(21) Appl. No.: 11/576,326

(22) PCT Filed: Sep. 30, 2005

(86) PCT No.: PCT/US2005/035171
§ 371 (c)(1),
(2), (4) Date: Dec. 21, 2007

(87) PCT Pub. No.: WO2006/039475
PCT Pub. Date: Apr. 13, 2006

(65) Prior Publication Data
US 2008/0119574 A1    May 22, 2008

Related U.S. Application Data

(60) Provisional application No. 60/614,057, filed on Sep. 30, 2004.

(51) Int. Cl.
*C02F 1/10* (2006.01)
*C07C 27/00* (2006.01)

(52) U.S. Cl. ............ 210/774; 95/254; 96/155; 96/202; 96/218; 210/175; 210/180; 210/195.1; 210/259; 210/749; 210/805; 210/806; 518/700; 518/705

(58) Field of Classification Search ............ 95/241, 95/254, 263; 96/218, 202, 155; 208/46, 208/49, 133, 950; 196/46; 210/175, 180, 210/194, 774, 805, 749, 767, 806, 908, 188, 210/195.1, 258, 259; 518/700–705, 708, 518/711, 722, 726
See application file for complete search history.

(56) References Cited

U.S. PATENT DOCUMENTS

| | | | |
|---|---|---|---|
| 2,741,649 A * | 4/1956 | Brooke et al. | 208/18 |
| 2,792,293 A | 5/1957 | Markert et al. | |
| 2,968,612 A * | 1/1961 | Loughran et al. | 208/136 |
| 4,808,764 A | 2/1989 | Fremuth et al. | |
| 4,814,156 A | 3/1989 | Pinto | |
| 5,008,088 A | 4/1991 | Fremuth et al. | |
| 5,041,144 A | 8/1991 | Lath | |
| 5,744,067 A | 4/1998 | Jahnke | |
| 5,958,107 A | 9/1999 | Greenwalt | |

(Continued)

FOREIGN PATENT DOCUMENTS
WO    WO 2004/041716    *    5/2004

*Primary Examiner* — Joseph Drodge
(74) *Attorney, Agent, or Firm* — Rothwell, Figg, Ernst & Manbeck, P.C.

(57) ABSTRACT

The present invention provides an apparatus for recovering organic compounds from plant waste water. A saturator (10) is coupled to a feed gas stream (70) and a heated makeup water stream (54) which includes recoverable organic compounds. The saturator provides a saturated feed gas stream (70) which includes feed gas, steam and recovered organic compounds. A pump (30) recycles saturator water (56) and the makeup water stream (50) is added to that recycle stream (54).

18 Claims, 2 Drawing Sheets

U.S. PATENT DOCUMENTS

| | | |
|---|---|---|
| 6,225,358 B1 | 5/2001 | Kennedy |
| 6,262,131 B1 * | 7/2001 | Arcuri et al. .................. 518/700 |
| 6,370,880 B1 | 4/2002 | Smith et al. |
| 6,525,104 B2 * | 2/2003 | Abbott .......................... 518/704 |
| 6,564,580 B2 | 5/2003 | Bowen et al. |
| 7,087,652 B2 * | 8/2006 | Abbott et al. ................. 518/700 |
| 2002/0177629 A1 * | 11/2002 | O'Beck et al. ................ 518/703 |
| 2005/0131086 A1 * | 6/2005 | Kohler et al. ................. 518/726 |

\* cited by examiner

RECOVERY OF ORGANIC COMPOUNDS USING A SATURATOR

CROSS-REFERENCE TO RELATED APPLICATIONS

The present application claims priority to U.S. Provisional Application Ser. No. 60/614,057, filed on Sep. 30, 2004, which is incorporated herein by reference in its entirety.

FIELD OF THE INVENTION

The present invention relates to organic compound recovery processes, and, in particular, to a process for recovering organic compounds using a saturator.

BACKGROUND OF THE INVENTION

In a Gas-to-Liquids (GTL) plant, a Fischer-Tropsch process may be used to produce waxy hydrocarbons (typically called Syncrude) which are then converted, or upgraded, into various GTL fuels downstream, including, for example, diesel, naphtha, etc. Unfortunately, the Fischer-Tropsch process also produces waste water, which contains organic compounds, such as hydrocarbons, alcohols, acids, etc. This effluent must be treated to remove the organic compounds—thereby increasing overall production costs.

In one example, a Fischer-Tropsch reactor is fed with synthesis gas, which is a mixture of hydrogen and carbon monoxide. While synthesis gas may be generated using a number of different schemes, hydrocarbon feedstock, such as natural gas, is typically fed into a synthesis gas reactor, or reformer, which produces synthesis gas for the Fischer-Tropsch reactor.

The reformer requires steam for the reforming reactions, and this steam may be introduced into the hydrocarbon feedstock, for example, by a steam header and/or steam that is generated within a saturator. Of course, makeup water must be supplied to produce this steam—thereby increasing overall production costs as well.

SUMMARY OF THE INVENTION

Embodiments of the present invention provides an apparatus for recovering organic compounds from plant waste water. A saturator is coupled to a feed gas stream and a heated makeup water stream which includes recoverable organic compounds. The saturator provides a saturated feed gas stream which includes feed gas, steam and recovered organic compounds. A pump recycles saturator water and the makeup water stream is added to that recycle stream.

BRIEF DESCRIPTION OF THE DRAWINGS

The above and other advantages of this invention will become more apparent by the following description of invention and the accompanying drawings.

DETAILED DESCRIPTION

Figure 1:
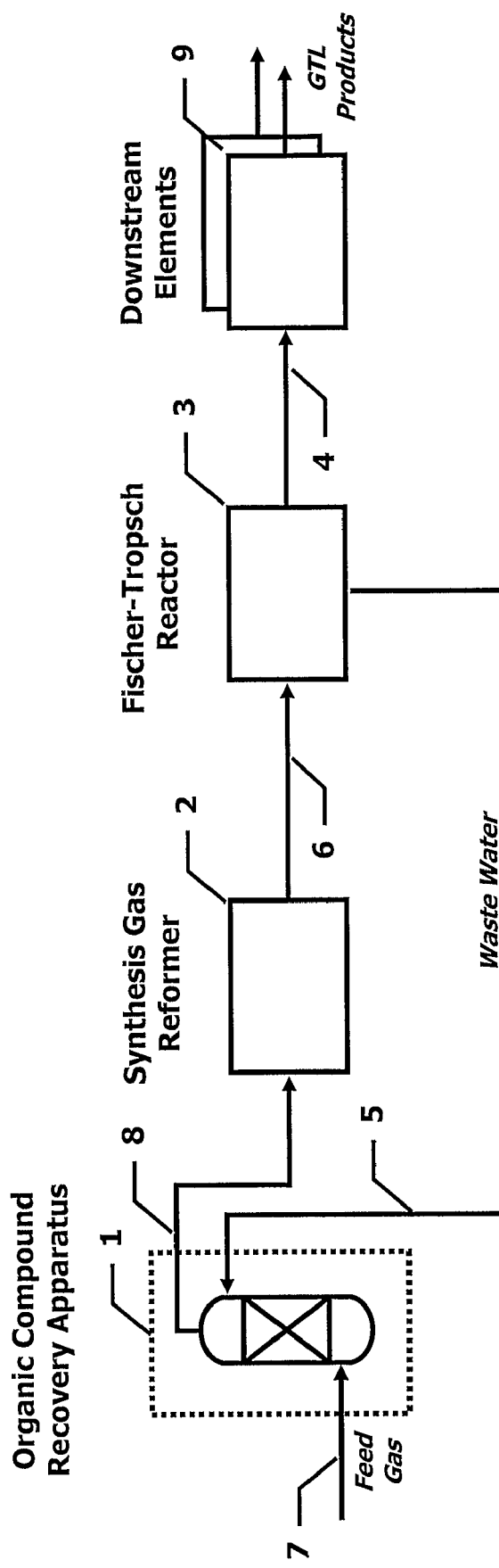
FIG. 1 is a schematic diagram depicting, generally, a GTL process in accordance with an embodiment of the present invention.

FIG. 1 is a schematic diagram depicting, generally, a GTL process in accordance with an embodiment of the present invention.

Organic compound recovery apparatus 1 provides saturated feed gas 8 to reformer 2, which produces synthesis gas 6 for Fischer-Tropsch reactor 3, which, in turn, produces hydrocarbons 4 and waste water 5. Downstream processing elements 9 convert hydrocarbons 4 into various products, including, for example, diesel, naphtha, etc. Waste water 5 is recycled back to organic compound recovery apparatus 1, which vaporizes the organic compounds, such as hydrocarbons, alcohols, acids, etc., within waste water 5, mixes them with feed gas 7 and forms saturated feed gas 8. Waste water containing organic compounds from other processes may be recycled to the saturator as well.

Advantageously, due to the presence of recovered organic compounds, such as hydrocarbons, alcohols, acids, etc., within saturated feed gas 8, reformer 2 produces more synthesis gas 6 than would otherwise be produced for a given amount of feed gas 7. Accordingly, overall production costs are commensurately reduced. Additionally, due the recovery of organic compounds, such as hydrocarbons, alcohols, acids, etc., from waste water 5, a much smaller volume of effluent needs to be treated, which also reduces overall production costs.

Figure 2:
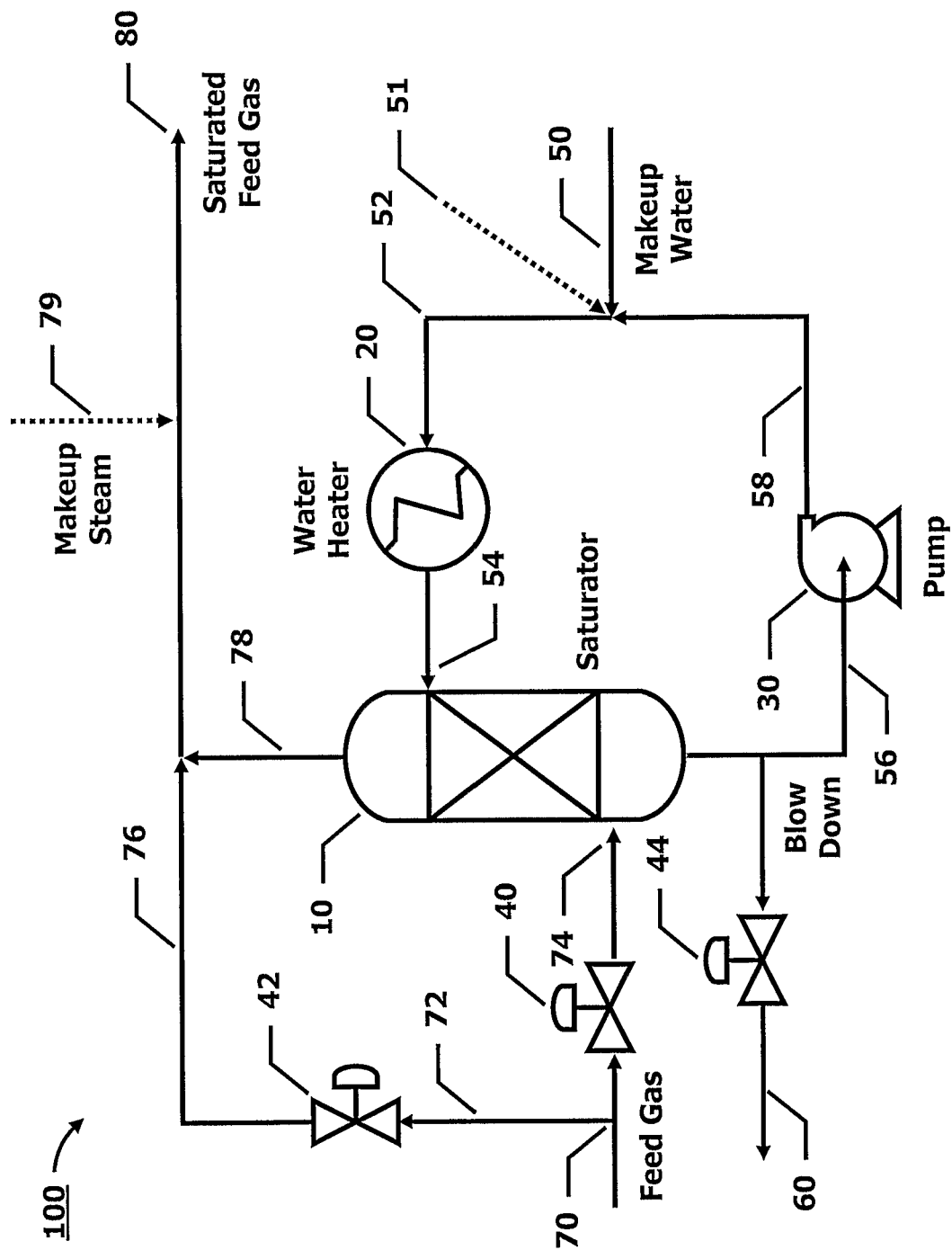
FIG. 2 is a schematic diagram depicting an organic compound recovery process in accordance with an embodiment of the present invention.

FIG. 2 is a schematic diagram depicting an organic compound recovery process in accordance with an embodiment of the present invention.

Organic compound recovery apparatus 100 recovers organic compounds, such as hydrocarbons, alcohols (C1 to C8), acids (formic, acetic acids, propionic, n-butyric, etc.), etc., from any aqueous stream, generally, and from Fischer-Tropsch reactor waste water, specifically, and includes saturator 10, water heater 20, pump 30, feed gas valve 40, feed gas bypass valve 42, saturator blow down valve 44 and various interconnections. With respect to the elements identified in FIG. 1, waste water 5 is provided to organic compound recovery apparatus 100 as makeup water stream 50, feed gas 7 is provided to organic compound recovery apparatus 100 as feed gas stream 70, and saturated feed gas stream 80 is provided to reformer 2 as saturated feed gas 8.

Natural gas, such as methane, ethane, propane, etc., or any other hydrocarbon, is introduced into organic compound recovery apparatus 100 as feed gas stream 70. In an exemplary embodiment, feed gas stream 70 is a mixture of various components including, but not limited to, hydrogen, nitrogen, methane and ethane, having flow rates of approximately 700, 1900, 32,600 and 138 kg-mole/hr, respectively, yielding a total mass rate of approximately 582,200 kg/hr. In this embodiment, feed gas stream 70 is introduced at approximately 375° C. and 43 barg.

In one embodiment, feed gas valve 40 and feed gas bypass valve 42 are controlled such that all of the feed gas stream 70 enters saturator 10 as feed gas stream 74 (i.e., non-bypass operation). In another embodiment, feed gas valve 40 and feed gas bypass valve 42 are controlled such that one portion of the feed gas stream 70 enters saturator 10 (i.e., feed gas stream 74), while another portion bypasses saturator 10 (i.e., bypassed feed gas stream 76) to be mixed with saturator overhead stream 78 to form saturated feed gas stream 80 (i.e., bypass operation). Advantageously, bypassing a portion of feed gas stream 70 increases the operating temperature of saturator 10, thereby increasing the recovery of organic compounds from makeup water 50 for a given amount of heat input, as discussed in greater detail below.

During bypass operation, in the exemplary embodiment, approximately 60% of feed gas stream 70 is diverted by feed gas bypass valve 42 to form bypassed feed gas stream 76. The flow rates of the hydrogen, nitrogen, methane and ethane are correspondingly reduced to approximately 425, 1140, 19,500 and 83 kg-mole/hr, respectively, yielding a total mass rate of approximately 350,000 kg/hr. In this embodiment, bypassed feed gas stream 76 is maintained at 375° C. and approximately 43 barg. Similarly, approximately 40% of feed gas stream 70 enters saturator 10 through feed gas bypass valve 40 as feed gas stream 74. The flow rates of the hydrogen, nitrogen, methane and ethane are correspondingly reduced to approximately 280, 760, 13,000 and 55 kg-mole/hr, respectively, yielding a total mass rate of approximately 233,000 kg/hr. In this embodiment, the temperature of feed gas stream 74 is reduced to 103° C. but the pressure is maintained at approximately 43 barg.

Feed gas stream 74 enters saturator 10 and flows upward through the vessel or column containing, for example, packing or trays. Makeup water stream 50, together with recycle water stream 58, are heated by water heater 20 and introduced into saturator 10 as heated water stream 54. In the exemplary embodiment, the mass rate, temperature and pressure of makeup water stream 50 are approximately 600,000 kg/hr, 65° C. and 52 barg, respectively; the mass rate, temperature and pressure of recycle water stream 58 are approximately 4,600,000 kg/hr, 195° C. and 50 barg, respectively; and the mass rate, temperature and pressure of heated water stream 54 are approximately 5,200,000 kg/hr, 245° C. and 49 barg, respectively. As the hydrocarbon feedstock vapor flows upward, heated water stream 54 is sprayed downward, thereby saturating the hydrocarbon feedstock vapor with steam. In addition to water evaporation, some of the volatile components present within heated water stream 54, such as, for example, hydrocarbons, alcohols (C1 to C8), acids, etc., also vaporize, resulting in a saturator overhead stream 78 that includes not only the hydrocarbon feedstock but also recovered organic compounds.

In an embodiment, additional water may be provided to saturator 10 via additional makeup water stream 51, which may be added to makeup water stream 50 and recycle water stream 58 prior to heating. Excess water exits saturator 10, where it is recycled via pump 30 and then mixed with makeup water 50. Saturator blow down valve 44 controls the quality of the recycled water. For example, saturator blow down valve 44 may be cycled periodically to purge some of the water from saturator 10, while in another example, saturator blow down valve 44 may be controlled to provide a predetermined water flow rate on a continuous basis. In the exemplary embodiment, recycle water stream 56 exits saturator 10 at approximately 4,600,000 kg/hr, 195° C. and 43 barg. In addition to water heater 20, heat may be provided to saturator 10 using a variety of mechanisms, including, for example, heat recovered elsewhere in the process, external heat sources, etc.

During non-bypass operation, the saturator overhead stream 78 is provided directly to synthesis gas reformer 2 as saturated feed gas stream 80. In the exemplary embodiment, saturated feed gas stream 80 is a mixture of various components including, but not limited to, hydrogen, carbon monoxide, carbon dioxide, nitrogen, methane, ethane, propane, n-butane, water, ammonia, methanol, ethanol, propanol, butanol, pentanol, hexanol, heptanol, octanol, formic acid and acetic acid, having flow rates of approximately 720, 1, 145, 1900, 32,600, 138, 1, 6, 32,400, 19, 117, 127, 45, 6, 2, 1, 0.5, 0, 20 and 6 kg-mole/hour, respectively, yielding a total mass rate of approximately 1,200,000 kg/hr. In this embodiment, saturated feed gas stream 80 is provided to reformer 2 at approximately 210° C. and 42 barg.

However, if the operating temperature inside saturator 10 is not high enough, some of the organic compounds that are present in heated water stream 54 may not vaporize and are, accordingly, not recovered. Consequently, bypassing a portion of feed gas stream 70 around saturator 10 reduces the amount of input feed gas (i.e., feed gas stream 74), thereby increasing the operating temperature of saturator 10 for a given heat input. The increase in operating temperature allows more organic compounds, such as hydrocarbons, alcohols, acids, etc., within heated water stream 54 to vaporize, advantageously increasing the amount of organic compounds recovered from heated water stream 54. Bypassed feed gas stream 76 is then mixed with saturator overhead stream 78 to provide the required saturated feed gas 80 flowrate to reformer 2.

During bypass operation, in the exemplary embodiment, saturated overhead stream 78 is a mixture of various components including, but not limited to, hydrogen, carbon monoxide, carbon dioxide, nitrogen, methane, ethane, propane, n-butane, water, ammonia, methanol, ethanol, propanol, butanol, pentanol, hexanol, heptanol, octanol, formic acid and acetic acid, having flow rates of approximately 295, 1, 150, 760, 13,000, 55, 1, 6, 33,500, 24, 115, 130, 50, 8, 4, 2, 1, 1, 20 and 6 kg-mole/hour, respectively, yielding a total mass rate of approximately 860,000 kg/hr. In this embodiment, saturated overhead stream 78 exits saturator 10 at approximately 230° C. and 42 barg.

Saturated overhead stream 78 is then mixed with bypassed feed gas stream 76 to form saturated feed gas stream 80. In the exemplary embodiment, saturated feed gas stream 80 is a mixture of various components including, but not limited to, hydrogen, carbon monoxide, carbon dioxide, nitrogen, methane, ethane, propane, n-butane, water, ammonia, methanol, ethanol, propanol, butanol, pentanol, hexanol, heptanol, octanol, formic acid and acetic acid, having flow rates of approximately 720, 1, 150, 1,900, 32,600, 138, 1, 6, 33,500, 24, 115, 130, 50, 8, 4, 2, 1, 1, 20, and 6 kg-mole/hour, respectively, yielding a total mass rate of approximately 1,200,000 kg/hr. In this embodiment, saturated feed gas stream 80 is provided to reformer 2 at approximately 275° C. and 42 barg.

The amount of bypassed feed gas may be automatically controlled in a variety of ways, including, for example, controlling the steam to gas (S/G) ratio of the saturator overhead stream 78, controlling the operating temperature of saturator 10, etc. In an alternative embodiment, makeup steam 79 may be mixed with saturated feed gas stream 80 to achieve the desired steam to gas ratio.

While this invention has been described in conjunction with specific embodiments thereof, many alternatives, modifications and variations will be apparent to those skilled in the art. Accordingly, the preferred embodiments of the invention as set forth herein, are intended to be illustrative, not limiting. Various changes may be made without departing from the true spirit and full scope of the invention as set forth herein.

What is claimed is:

1. An apparatus for recovering organic compounds from plant waste water, comprising:
   a feed gas stream;
   a makeup water stream including recoverable organic compounds;
   a water heater coupled to the makeup water stream and a recycle water stream;
   a saturator, coupled to the feed gas stream and the water heater, to separately provide:
   a saturated feed gas stream, wherein said saturated feed gas stream contains feed gas, steam and organic compounds recovered from the makeup water stream, and
   b) the recycle water stream;
   a pump coupled to the recycle water stream;

a first valve, coupled to the feed gas stream and the saturator, to provide a portion of the feed gas stream to the saturator; and a bypass valve, coupled to the feed gas stream and the saturated feed gas stream, to selectively divert a remaining predetermined portion of the feed gas stream around the saturator, wherein, when the remaining predetermined portion of the feed gas stream is selectively diverted around the saturator and mixed with the saturated feed gas stream in a gas conduit while said first valve continues to provide a predetermined portion of feed gas stream to said saturator, the saturator operating temperature increases and the amount of organic compounds recovered from the makeup water increases.

2. The apparatus of claim 1, wherein the feed gas stream includes natural gas.

3. The apparatus of claim 2, wherein the makeup water is provided by a Fischer-Tropsch reactor.

4. The apparatus of claim 3, wherein the recoverable organic compounds include heavy hydrocarbons, C1 to C8 alcohols and acids, the acids including formic, acetic, propionic and n-butyric acids.

5. The apparatus of claim 1, wherein said makeup water stream is coupled to a recycle water loop feeding makeup water to said saturator and removing water from said saturator.

6. A system for recovering organic compounds within a gas-to-liquids plant, comprising:
a Fischer-Tropsch reactor having a waste water stream including recoverable organic compounds;
a synthesis gas reformer coupled to the Fischer-Tropsch reactor; and
an organic compound recovery apparatus configured to provide a saturated feed gas stream, which is formed in a saturator of the organic compound recovery apparatus, to the synthesis gas reformer,
wherein said organic compound recovery apparatus is coupled to a feed gas stream, the Fischer-Tropsch reactor waste water stream and the synthesis gas reformer, and wherein said saturated feed gas stream contains feed gas, steam and organic compounds recovered from the Fischer-Tropsch reactor waste water stream,
and wherein said waste water stream is fed to said organic compound recovery apparatus as makeup water, wherein said makeup water is coupled to a recycle water loop feeding makeup water to said saturator and removing water from said saturator.

7. The system of claim 6, wherein the feed gas stream includes natural gas.

8. The system of claim 6, wherein the recoverable organic compounds include heavy hydrocarbons, C1 to C8 alcohols, and acids, the acids including formic, acetic, propionic and n-butyric acids.

9. The system of claim 6, wherein the organic compound recovery apparatus includes:
a water heater coupled to the Fischer-Tropsch reactor waste water stream and a recycle water stream;
a saturator, coupled to the feed gas stream, the recycle water stream and the water heater, to provide the saturated feed gas stream and the recycle water stream; and
a pump coupled to the recycle water stream.

10. The system of claim 9, further comprising:
a first valve, coupled to the feed gas stream and the saturator, to provide a portion of the feed gas stream to the saturator; and a bypass valve, coupled to the feed gas stream and the saturated feed gas stream, to selectively divert a remaining predetermined portion of the feed gas stream around the saturator,
wherein, when the remaining predetermined portion of the feed gas stream is selectively diverted around the saturator and mixed with the saturated feed gas stream in a gas conduit while said first valve continues to provide a predetermined portion of feed gas stream to said saturator, the saturator operating temperature increases and the amount of organic compounds recovered from the Fischer-Tropsch waste water stream increases.

11. The system of claim 6, further comprising an additional makeup water stream coupled to the organic compound recovery apparatus.

12. The system of claim 11, wherein the additional makeup water stream includes recoverable organic compounds.

13. The system of claim 6, further comprising a substitute makeup water stream, including recoverable organic compounds, coupled to the organic compound recovery apparatus to replace of the Fischer-Tropsch reactor waste water stream.

14. A method for recovering organic compounds from plant waste water, comprising:
providing a feed gas stream to a saturator;
mixing a makeup water stream generated by a hydrocarbon producing reactor, including recoverable organic compounds, with a recycle water stream;
heating the mixed makeup water stream;
providing the heated makeup water stream to the saturator;
generating a saturated feed gas stream including feed gas, steam and organic compounds recovered from the makeup water stream;
generating the recycle water stream;
selectively bypassing a selected portion of the feed gas stream around the saturator while continuing to provide a predetermined amount of feed gas stream to the saturator to increase the operating temperature of the saturator and to increase the amount of organic compounds recovered from the makeup water stream; and
mixing the bypassed portion of the feed gas stream with the saturated feed gas stream.

15. The method of claim 14, wherein the feed gas stream includes natural gas.

16. The method of claim 15, wherein the makeup water stream is provided by a Fischer-Tropsch reactor.

17. The method of claim 16, wherein the recoverable organic compounds include heavy hydrocarbons, C1 to C8 alcohols and acids, the acids including formic, acetic, propionic and n-butyric acids.

18. The method of claim 15, further comprising mixing an additional makeup water stream with said makeup water stream prior to said heating step.

* * * * *